US011963666B2

United States Patent
Atarot et al.

(10) Patent No.: US 11,963,666 B2
(45) Date of Patent: *Apr. 23, 2024

(54) OVERALL ENDOSCOPIC CONTROL SYSTEM

(71) Applicant: Asensus Surgical Europe S.à.R.L., Lugano (CH)

(72) Inventors: Gal Atarot, Kfar Saba (IL); Yaron Levinson, Haifa (IL)

(73) Assignee: Asensus Surgical Europe S.à.R.L., Lugano (CH)

( * ) Notice: Subject to any disclaimer, the term of this patent is extended or adjusted under 35 U.S.C. 154(b) by 416 days.

This patent is subject to a terminal disclaimer.

(21) Appl. No.: 17/039,856

(22) Filed: Sep. 30, 2020

(65) Prior Publication Data

US 2021/0015351 A1 Jan. 21, 2021

Related U.S. Application Data

(63) Continuation of application No. 14/380,086, filed as application No. PCT/IL2013/050216 on Mar. 7, 2013, now Pat. No. 10,898,064.

(Continued)

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00004* (2013.01); *A61B 1/00009* (2013.01);
(Continued)

(58) Field of Classification Search
CPC ... A61B 1/0005; A61B 1/016; A61B 1/00025; A61B 1/00036; A61B 1/00039;
(Continued)

(56) References Cited

U.S. PATENT DOCUMENTS

2008/0159653 A1* 7/2008 Dunki-Jacobs .......... A61B 1/04
382/293
2008/0281467 A1* 11/2008 Pinter .................... H04L 67/025
901/50

(Continued)

*Primary Examiner* — Timothy J Neal
*Assistant Examiner* — William B Chou

(57) ABSTRACT

The present invention provides a system for controlling an endoscope, comprising a. an endoscope adapted to provide real time images of FOV within a body cavity; said FOV defines FOVx-axis, FOVy-axis and FOVz-axis, b. a maneuvering system for maneuvering said endoscope; said maneuvering system defines an X-axis, a y-axis; and, a z-axis; c. control means adapted to receive commands of motions from a user to maneuver said endoscope; and d. a data processing system in communication with said control means, adapted to instruct said maneuvering system to maneuver said endoscope according to said commands of motions; wherein said data control means instructs said maneuvering system to maneuver said endoscope according to said commands of motions relative to said FOVx-axis, said FOVy-axis and said FOVz-axis, regardless of said X-axis, said y-axis and said z-axis as defined by said maneuvering system.

8 Claims, 7 Drawing Sheets

Related U.S. Application Data

(60) Provisional application No. 61/607,661, filed on Mar. 7, 2012.

(51) Int. Cl.
| | | |
|---|---|---|
| *A61B 34/35* | (2016.01) | |
| *A61B 90/00* | (2016.01) | |
| *B25J 13/08* | (2006.01) | |
| *B25J 19/02* | (2006.01) | |
| *A61B 17/00* | (2006.01) | |
| *A61B 34/00* | (2016.01) | |
| *A61B 34/20* | (2016.01) | |

(52) U.S. Cl.
CPC ........ *A61B 1/0004* (2022.02); *A61B 1/00147* (2013.01); *A61B 34/35* (2016.02); *A61B 90/37* (2016.02); *B25J 13/08* (2013.01); *B25J 19/021* (2013.01); *A61B 2017/00026* (2013.01); *A61B 2017/00075* (2013.01); *A61B 2017/00084* (2013.01); *A61B 2034/2048* (2016.02); *A61B 2034/741* (2016.02); *A61B 2034/742* (2016.02)

(58) Field of Classification Search
CPC ............ A61B 1/00147; A61B 1/00149; A61B 1/0016; A61B 5/061; A61B 5/065; A61B 34/10; A61B 34/20; A61B 2034/2065; A61B 2034/107; A61B 2034/2046; A61B 2034/2068; A61B 2034/2072; A61B 2034/2074

See application file for complete search history.

(56) References Cited

U.S. PATENT DOCUMENTS

| | | | |
|---|---|---|---|
| 2009/0055023 A1* | 2/2009 | Walters | H04N 7/141 901/1 |
| 2010/0234857 A1* | 9/2010 | Itkowitz | G09B 23/285 700/259 |
| 2015/0065793 A1* | 3/2015 | Diolaiti | A61B 1/00149 600/102 |
| 2015/0094856 A1* | 4/2015 | Popovic | B25J 9/1697 382/103 |
| 2017/0156808 A1* | 6/2017 | Auld | A61B 34/70 |
| 2018/0303558 A1* | 10/2018 | Thomas | A61B 34/20 |
| 2019/0056693 A1* | 2/2019 | Gelman | G06T 19/006 |

* cited by examiner

OVERALL ENDOSCOPIC CONTROL SYSTEM

FIELD OF THE INVENTION

The present invention generally pertains to a system and method for controlling an endoscope.

BACKGROUND OF THE INVENTION

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and is not available in all hospitals. During lap aroscopic surgery it is often required to shift the spatial placement of the endoscope in order to present the surgeon with the optimal view. Conventional laparoscopic surgery makes use of either human assistants that manually shift the instrumentation or alternatively robotic automated assistants (such as JP patent No. 06063003).

In lap aroscopic surgery, the surgeon performs the operation through small holes using long instruments and observing the internal anatomy with an endoscope camera. The endoscope is conventionally held by a camera assistant since the surgeon must perform the operation using both hands. The surgeon's performance is largely dependent on the camera position relative to the instruments and on a stable image shown at the monitor; also the picture shown must be in the right orientation. The main problem is that it is difficult both for the assistant to keep the endoscope in the right spatial position, and for the assistant to hold the endoscope steadily, keeping the field in the right orientation. To overcome these problems, several new technologies have been developed, using robots to hold the endoscope while the surgeon performs the procedure, e.g., Lapman, Endoassist etc. But these technologies are expensive, difficult to install, uncomfortable to use, limit the dexterity of the surgeon and have physical dimensions much larger that all the other operating tools. Relative to the required action, they also require a large region to be kept free for their movement and have several arms, moving around different axes. Another robot, LER (which was developed by the TIMC-GMCAO Laboratory), US. Patent application No. 200/6100501 consists of a compact camera-holder robot that rests directly on the patient's abdomen and an electronic box containing the electricity supply and robot controllers. LER has relatively small dimensions but has a 110 mm diameter base ring that must be attached to, or be very close to, the patient's skin. This ring occupies a place over the patient's body, thus limiting the surgeon's activities: other trochars can not be placed there, whether or not the surgeon would prefer this, possibly changing the surgeon's usual method of carrying out the procedure, and sometimes forcing the setup process to be as long as 40 minutes. Also, the LER has only 3 degrees of freedom and is unable to control the orientation of the picture shown to surgeon (the LER cannot rotate the endoscope around its longitudinal axis).

However, even the improved technologies still limit the dexterity of the surgeon and fail to provide the necessary four degrees of freedom. Another disadvantage of these technologies is that they lack the ability to control fully both the spatial position of the endoscope tube and its orientation during the laparoscopic surgery, so that the surgeon may view any desired area within the working envelope in the body being operated on.

Therefore, there is still a long felt need for a camera holder that will hold the endoscope steady and that will allow full control of the endoscope in all four degrees of freedom, without limiting the dexterity of the surgeon. Furthermore, there is also a long felt need for a camera holder that will provide the ability to control the spatial orientation of an endoscope tube, so that the surgeon may reach any desired area within the working envelope in operated body and may view that area from any desired angle However, conventional endoscopic systems either rely on manual control requiring a user to reposition the endoscope manually, or they use absolute positioning. Manual control systems either require the surgeon to pause the operation in order to reposition the endoscope or require an additional operative in the theater to control the position of the endoscope, while absolute positioning systems can require counter-intuitive manipulation of a control apparatus. Counter-intuitive manipulation of a control apparatus will occur, for example, if the endoscopic camera axes are not parallel to the axes of the absolute positioning system. If, for example, the endoscopic camera axes are anti-parallel to the axes of the absolute positioning system, to move the field of view to the left, the control system must be commanded to move the endoscope to the right, and vice versa, requiring the surgeon to remember the relative position of the camera and the positioning system axes.

It is therefore a long felt need to provide a system for controlling the position and motion of an endoscope which does not normally require manual control and which does not require counter-intuitive manipulation of control apparatus.

SUMMARY OF THE INVENTION

It is an object of the present invention to disclose a system for controlling an endoscope.

It is another object of the present invention to disclose a system for controlling an endoscope, comprising a. an endoscope adapted to provide real time images of an FOV within a body cavity; the FOV defines at least two axes selected from a group consisting of FOVx-axis, FOVy-axis and FOVz-axis and any combination thereof, such that at least two axes selected from the FOVx-axis, the FOVy-axis, the FOVz-axis and any combination thereof are adapted to be real time updated as the endoscope moves and the FOV changes; the endoscope is characterized by a spatial location; the spatial location is real-time updated as the endoscope moves;

b. a maneuvering system for maneuvering the endoscope in at least two DOF; the maneuvering system defines a constant x-axis, a constant y-axis and a constant z-axis;

c. control means adapted to receive commands of motions from a user to maneuver the endoscope; and d. a data processing system in communication with the control means, adapted to instruct the maneuvering system to maneuver the endoscope according to the commands of motions;

wherein the data control means instructs the maneuvering system to maneuver the endoscope according to the commands of motions relative to at least two axes selected from the FOVx-axis, the FOVy-axis and the FOVz-axis and any combination thereof, as real time displayed in the image, regardless of the spatial location of the endoscope and of the x-axis, the y-axis and the z-axis as defined by the maneuvering system; further wherein the data processing system is adapted to convert the commands of motions relative to at least two axes selected from the FOVx-axis, the FOVy-axis, the FOVz-axis and any combination thereof to commands of motions relative to the x-axis, the y-axis and the z-axis, such that the maneuvering system is adapted to move the endoscope relative to the x-axis, the y-axis and the z-axis to result in the motions as commanded relative to at least two axes selected from the FOVx-axis, the FOVy-axis, FOVz-axis and any combination thereof.

It is another object of the present invention to disclose the system as defined above, wherein the data control means instructs the maneuvering system to maneuver the endoscope according to the commands of motions relative to at least two axes selected from the FOVx-axis, the FOVy-axis and the FOVz-axis and any combination thereof, as real time displayed in the image, regardless of the orientation of the camera within the endoscope with respect to the endoscope.

It is another object of the present invention to disclose the system as defined above, 1, wherein the data control means instructs the maneuvering system to maneuver the endoscope according to the commands of motions relative to at least two axes selected from the FOVx-axis, the FOVy-axis and the FOVz-axis and any combination thereof, as real time displayed in the image, regardless of the angular orientation of the camera within the endoscope with respect to the endoscope It is another object of the present invention to disclose the system as defined above, wherein the data control means instructs the maneuvering system to maneuver the endoscope according to the commands of motions relative to at least two axes selected from the FOVx-axis, the FOVy-axis and the FOVz-axis and any combination thereof, as real time displayed in the image, regardless of the orientation of the endoscope with respect to the maneuvering system.

It is another object of the present invention to disclose the system as defined above, wherein the control means are adapted to receive commands of motions to maneuver at least one surgical tool within the FOV.

It is another object of the present invention to disclose the system as defined above, wherein the data control means instructs the maneuvering system to maneuver the surgical tool according to the commands of motions relative to the FOVx-axis, FOVy-axis, FOVz-axis, as real time displayed in the image, regardless of the x-axis, the y-axis and the z-axis as defined by the maneuvering system; further wherein the data processing system is adapted to convert the commands of motions relative to the FOVx-axis, FOVy-axis, FOVz-axis to commands of motions relative to the x-axis, the y-axis and the z-axis.

It is another object of the present invention to disclose the system as defined above, wherein the control means comprises at least one joystick unit in communication with the maneuvering system, adapted to operate the maneuvering system.

It is another object of the present invention to disclose the system as defined above, wherein the joystick unit is wearable by a user of the system.

It is another object of the present invention to disclose the system as defined above, wherein the joystick unit is coupled to at least one surgical tool used in the medical procedure.

It is another object of the present invention to disclose the system as defined above, wherein the at least one surgical tool is the endoscope.

It is another object of the present invention to disclose the system as defined above, wherein the movement of the joystick is proportional to the movement of the endoscope.

It is another object of the present invention to disclose the system as defined above, wherein the joystick unit is a force joystick.

It is another object of the present invention to disclose the system as defined above, wherein the joystick unit comprises a base and lever coupled to the base, such that movement of the lever results in movement of the endoscope; further wherein the movement of the lever is proportional to the movement of the endoscope.

It is another object of the present invention to disclose the system as defined above, wherein the joystick unit comprises a base and a button jointly connected to the base, such that movement of the button results in movement of the endoscope; further wherein the movement of the button is proportional to the movement of the endoscope.

It is another object of the present invention to disclose the system as defined above, wherein the joystick unit comprises a touchscreen, such that a touch and a movement on the touchscreen results in movement of the endoscope; further wherein the touch and movement on the touchscreen is proportional to the movement of the endoscope.

It is another object of the present invention to disclose the system as defined above, wherein the joystick unit comprises at least one sound sensor, adapted to sense predetermined sound patterns; the joystick unit adapted to operate the maneuvering system based on the predetermined sound patterns.

It is another object of the present invention to disclose the system as defined above, wherein the system directs the endoscope by using image information shown on the video screen without the help of assistants.

It is another object of the present invention to disclose the system as defined above, wherein, if the joystick unit's speed of motion is above a predetermined value, the endoscope's speed is at the predetermined value.

It is another object of the present invention to disclose the system as defined above, wherein the joystick unit additionally comprises n sensors, where n is an integer larger than one.

It is another object of the present invention to disclose the system as defined above, wherein the sensors are selected from a group consisting of a motion sensor, a heat sensor, an electric sensor, a sound sensor, a pressure sensor, an optical sensor and any combination thereof.

It is another object of the present invention to disclose the system as defined above, wherein at least one of the n sensors is activated in case of power failure.

It is another object of the present invention to disclose the system as defined above, wherein at least one of the n sensors is activated when the system is connected to power.

It is another object of the present invention to disclose the system as defined above, wherein the joystick unit is characterized by an external surface.

It is another object of the present invention to disclose the system as defined above, wherein the at least one motion sensor detects motion upon the external surface.

It is another object of the present invention to disclose the system as defined above, wherein the at least one motion sensor detects motion perpendicular to the external surface.

It is another object of the present invention to disclose the system as defined above, wherein the at least one heat sensor is adapted to sense temperatures in the range of about 35 to about 42 degrees.

It is another object of the present invention to disclose the system as defined above, wherein the system is adapted to enable maneuvering of the endoscope at such times as the at least one heat sensor senses temperatures in the range of about 35 to about 42 degrees.

It is another object of the present invention to disclose the system as defined above, wherein the at least one heat sensor is adapted to provide thermal image; the at least one heat sensor is coupled to a processing unit adapted to provide the system user with the thermal image.

It is another object of the present invention to disclose the system as defined above, wherein the system is adapted to enable maneuvering of the endoscope at such times as analysis of the image by the processing unit detects the image of a human hand; further wherein the system is adapted to prevent maneuvering of the endoscope at such times when the analysis of the image by the processing unit fails to detect an image of a human hand.

It is another object of the present invention to disclose the system as defined above, wherein the at least one electric sensor is adapted to sense power failure.

It is another object of the present invention to disclose the system as defined above, wherein the at least one electric sensor is adapted to sense electric conductivity of a human body.

It is another object of the present invention to disclose the system as defined above, wherein the system is adapted to enable maneuvering of the endoscope at such times when the sensor senses the conductivity of the subject's body; further wherein the system is adapted to prevent maneuvering of the endoscope at such times as the sensor fails to sense the conductivity of the subject's body.

It is another object of the present invention to disclose the system as defined above, wherein the at least one sound sensor is adapted to sense at least one predetermined sound pattern.

It is another object of the present invention to disclose the system as defined above, wherein the endoscope is maneuverable according to the at least one predetermined sound pattern sensed by the at least one sound sensor.

It is another object of the present invention to disclose the system as defined above, wherein the at least one pressure sensor is adapted to sense pressure applied to the joystick unit.

It is another object of the present invention to disclose the system as defined above, wherein the pressure sensed by the at least one pressure sensor affects the maneuvering system in a manner selected from a group consisting of: when the pressure sensed by the at least one pressure sensor is above a predetermined value, the maneuvering system is activated; when the pressure sensed by the at least one pressure sensor is above a predetermined value, the maneuvering system is de-activated; and when the pressure sensed by the at least one pressure sensor is below a predetermined value, the maneuvering system is de-activated.

It is another object of the present invention to disclose the system as defined above, wherein the at least one optical sensor is adapted to sense visual changes according to at least one predetermined visual pattern.

It is another object of the present invention to disclose the system as defined above, wherein the endoscope is maneuverable according to the at least one predetermined visual pattern.

It is another object of the present invention to disclose the system as defined above, additionally comprising an interface system adapted to enable communication between the joystick unit and the maneuvering system.

It is another object of the present invention to disclose the system as defined above, wherein the communication means comprises a member selected from a group consisting of a wired communication means, a wireless communication means and any combination thereof.

It is another object of the present invention to disclose the system as defined above, wherein the maneuvering system comprises at least one second joystick unit adapted to zoom the endoscope by means of the maneuvering system.

It is another object of the present invention to disclose the system as defined above, wherein the second joystick unit is wearable by the system user.

It is another object of the present invention to disclose the system as defined above, wherein the second joystick unit is coupled to at least one surgical tool.

It is another object of the present invention to disclose the system as defined above, wherein the at least one surgical tool is the endoscope.

It is another object of the present invention to disclose the system as defined above, wherein a single device comprises the joystick unit and the second joystick unit.

It is another object of the present invention to disclose the system as defined above, wherein the at least one joystick unit is adapted to control and to direct the endoscope on the surgical tool via the maneuvering system.

It is another object of the present invention to disclose the system as defined above, wherein selection of the at least one surgical tool is obtained by activating the at least one joystick unit; further wherein the activation of the at least one joystick unit is obtained by depression of the joystick unit, voice activating the same, prolonged depression on the same, double clicking on the same and any combination thereof.

It is another object of the present invention to disclose the system as defined above, additionally comprising
  a. at least one wearable operator comprising at least one wireless transmitter, adapted to transmit a signal once the at least one wearable operator is activated; the at least one wearable operator is either wire or wirelessly in communication with at least one surgical instrument;
  b. at least one wireless receiver; adapted to receive the signal sent by the transmitter;
  c. at least one laparoscopy computerized system, in communication with the wireless receiver, adapted to provide a visual onscreen depiction of the at least one instrument to be selected following the activation of the at least one wearable operator; and,
  d. at least one video screen; wherein the system is adapted to control and to direct the endoscope via the laparoscopy computerized system and the maneuvering system on the instrument to be selected following the activation of the at least one wearable operator.

It is another object of the present invention to disclose the system as defined above, wherein the communication between the at least one of the wearable operators and the instrument is either wire or wirelessly coupling.

It is another object of the present invention to disclose the system as defined above, wherein the wearable operator is worn by the surgeon on a predetermined body part.

It is another object of the present invention to disclose the system as defined above, wherein the predetermined body part is selected from a group consisting of: the hand of the surgeon, at least one of the fingers of the surgeon, the thigh of the surgeon, the neck of the surgeon, at least one of the legs of the surgeon, the knee of the surgeon, the head of the surgeon and any combination thereof.

It is another object of the present invention to disclose the system as defined above, wherein the shape of the wearable operator is selected from a group consisting of a ring, a bracelet and any combination thereof.

It is another object of the present invention to disclose the system as defined above, wherein the wearable operator is coupled to a predetermined location on the instrument by means of an adaptor.

It is another object of the present invention to disclose the system as defined above, wherein the wearable operator is adjustable so as to fit the predetermined location of the different instruments, each of which is characterized by a different size and shape.

It is another object of the present invention to disclose the system as defined above, wherein the wearable operator comprises a body having at least two portions at least partially overlapping each other; the two portions are adapted to grasp and hold either the instrument or the predetermined body part there-between, such that a tight-fit coupling between the two portions and the instrument or the predetermined body part is obtained.

It is another object of the present invention to disclose the system as defined above, wherein one of the two portions is rotationally movable relative to the other, such that when the wearable operator is coupled to the instrument, fine-tuned movement of the two body portions is obtainable so as to provide the tight-fit coupling between the two portions and the instrument or the predetermined body part.

It is another object of the present invention to disclose the system as defined above, wherein the two portions are rotationally movable relative to each other, such that when the wearable operator is coupled to the instrument, fine-tuned movement of the two body portions is obtainable so as to provide the tight-fit coupling between the two portions and the instrument or the predetermined body part.

It is another object of the present invention to disclose the system as defined above, wherein the wearable operator comprises (a) at least one flexible and stretchable strip; and (b) loop-closing means adapted to close a loop with the at least one flexible and stretchable strip; the at least one flexible and stretchable strip and the loop-closing means are provided so as to fit the wearable operator to at least one selected from a group consisting of (a) the predetermined location of the different instruments; (b) the predetermined body part of the surgeon, each of which is characterized by a different size and shape.

It is another object of the present invention to disclose the system as defined above, wherein the flexible and stretchable strip is made of material selected from a group consisting of silicone, rubber and any combination thereof.

It is another object of the present invention to disclose the system as defined above, wherein the wireless transmitter is adapted to locate the position of at least one of the instruments.

It is another object of the present invention to disclose the system as defined above, wherein selection of the at least one instrument is obtained by activating the at least one wearable operator; further wherein the activation of the at least one wearable operator is obtained by depression on a predetermined location in the wearable operator, voice activating the same, prolonged depression on the same, double clicking on the same and any combination thereof.

It is another object of the present invention to disclose the system as defined above, wherein the laparoscopy computerized system directs the endoscope by using image information shown on the video screen without the help of assistants.

It is another object of the present invention to disclose the system as defined above, wherein the conventional laparoscopy computerized system comprises at least one surgical instrument spatial location software, adapted to locate the 3D spatial position of the at least one instrument; further wherein the conventional laparoscopy computerized system comprises at least one automated assistant maneuvering system; the automated assistant maneuvering system is coupled to the endoscope and is adapted to direct the endoscope to the at least one instrument, the instrument selected following the activation of the at least one wearable operator.

It is another object of the present invention to disclose the system as defined above, wherein each transmitted signal from the wearable operator and the wireless transmitter is matched to at least one of the instruments.

It is another object of the present invention to disclose the system as defined above, wherein velocity of the endoscope;s tip varies according to the closeness of the endoscope's tip to an object in the center of the FOV.

It is another object of the present invention to disclose the system as defined above, wherein the velocity of the endoscope's tip is proportional to distance between the endoscope's tip and the object the center of the FOV.

It is another object of the present invention to disclose the system as defined above, wherein the endoscope is an articulated endoscope.

It is another object of the present invention to disclose the system as defined above, wherein articulation of the articulated endoscope is controlled by the system.

It is another object of the present invention to disclose the system as defined above, wherein articulation of the articulated endoscope is controlled independently of the system.

It is another object of the present invention to disclose the system as defined above, wherein the endoscope is characterized by a pivoting point.

It is another object of the present invention to disclose the system as defined above, wherein the system automatically corrects for changes in the pivoting point of the endoscope.

It is another object of the present invention to disclose the system as defined above, wherein the control means is coupled to the endoscope maneuvering system via a link selected from a group consisting of: a wired link, a wireless link, and any combination thereof.

It is another object of the present invention to disclose the system as defined above, wherein the system maintains the center of the FOV unchanged during zooming, independent of the angle of the endoscope's tip with respect to the longitudinal axis of the endoscope.

It is another object of the present invention to disclose the system as defined above, wherein the system maintains the angle of the FOV unchanged during zooming.

It is another object of the present invention to disclose the system as defined above, wherein the system maintains the angle of the FOV unchanged during lateral motion.

It is another object of the present invention to disclose the system as defined above, wherein the angle of the endoscope's tip with respect to the longitudinal axis of the endoscope is not predetermined.

It is another object of the present invention to disclose the system as defined above, wherein the control means is adapted to be worn in conjunction with at least some portion of the body of a user.

It is another object of the present invention to disclose the system as defined above, wherein the portion of the body is selected from the group consisting of finger, arm, chest, head, neck, waist, hips, thighs, legs, and any combination thereof.

It is another object of the present invention to disclose the system as defined above, wherein the system automatically maintains the image unchanged by maneuvering the endoscope in response to uncommanded motion.

It is another object of the present invention to disclose the system as defined above, wherein the system automatically maintains the horizon of the image unchanged by maneuvering the endoscope in response to uncommanded motion.

It is another object of the present invention to disclose the system as defined above, wherein the system automatically maintains the horizon of the image unchanged during maneuvering of the endoscope.

It is another object of the present invention to disclose the system as defined above, wherein the system is adapted to track an object.

It is another object of the present invention to disclose the system as defined above, wherein the system is adapted to retain the object in the center of the FOV of the camera.

It is another object of the present invention to disclose the system as defined above, wherein the object is one of a group consisting of an organ, a vein, an artery, a ligament, a membrane, fat tissue, a medical tool, a scalpel, a forceps, a retractor, a swab, a clamp, and a needle.

It is another object of the present invention to disclose the system as defined above, wherein the system is adapted to maneuver a controlled object selected from a group consisting of an endoscope and a surgical tool in a manner selected from a group consisting of a discrete movement, a continuous movement and any combination thereof.

It is another object of the present invention to disclose a method for controlling an endoscope comprising steps of:
a. acquiring an endoscope adapted to provide real time images of FOV within a body cavity; the FOV defines at least two axes selected from a group consisting of FOVx-axis, FOVy-axis and FOVz-axis and any combination thereof, such that at least two axes selected from the FOVx-axis, the FOVy-axis, the FOVz-axis and any combination thereof are adapted to be real time updated as the endoscope moves and the FOV changes; the endoscope is characterized by a spatial location; the spatial location is real-time updated as the endoscope moves;
b. acquiring a maneuvering system for maneuvering the endoscope in at least two DOF; the maneuvering system defines a constant x-axis, a constant y-axis and a constant z-axis;
c. acquiring control means adapted to receive commands of motions from a user to maneuver the endoscope;
d. providing a data processing system in communication with the control means, adapted to instruct the maneuvering system to maneuver the endoscope according to the commands of motions;
e. converting the commands of motion relative to the FOVx-axis, the FOVy-axis and the FOVz-axis to commands of motions relative to the at least two axes selected from the FOVx-axis, the FOVy-axis and the FOVz-axis and any combination thereof, such that the maneuvering system is adapted to move the endoscope relative to the at least two axes selected from the FOVx-axis, the FOVy-axis and the FOVz-axis and any combination thereof so as to result in the motions as commanded relative to the FOVx-axis, the FOVy-axis and the FOVz-axis; and
f. maneuvering the endoscope according to the commands of motions relative to the FOVx-axis, the FOVy-axis and the FOVz-axis, as real time displayed in the image, regardless of the spatial location of the endoscope and of the at least two axes selected from the FOVx-axis, the FOVy-axis and the FOVz-axis and any combination thereof as defined by the maneuvering system.

It is another object of the present invention to disclose the method as defined above, additionally comprising a step of adapting the data control means to instruct the maneuvering system to maneuver the endoscope according to the commands of motions relative to at least two axes selected from the FOVx-axis, the FOVy-axis and the FOVz-axis and any combination thereof, as real time displayed in the image, regardless of the orientation of the camera within the endoscope with respect to the endoscope.

It is another object of the present invention to disclose the method as defined above, additionally comprising a step of adapting the data control means to instruct the maneuvering system to maneuver the endoscope according to the commands of motions relative to at least two axes selected from the FOVx-axis, the FOVy-axis and the FOVz-axis and any combination thereof, as real time displayed in the image, regardless of the angular orientation of the camera within the endoscope with respect to the endoscope It is another object of the present invention to disclose the method as defined above, additionally comprising a step of adapting the data control means to instruct the maneuvering system to maneuver the endoscope according to the commands of motions relative to at least two axes selected from the FOVx-axis, the FOVy-axis and the FOVz-axis and any combination thereof, as real time displayed in the image, regardless of the orientation of the endoscope with respect to the maneuvering system.

It is another object of the present invention to disclose the method as defined above, additionally comprising a step of adapting the control means to receive commands of motions to maneuver at least one surgical tool within the FOV.

It is another object of the present invention to disclose the method as defined above, additionally comprising a step of providing the data control means adapted to instruct the maneuvering system to maneuver the surgical tool according to the commands of motions relative to the FOVx-axis, FOVy-axis, FOVz-axis, as real time displayed in the image, regardless of the x-axis, the y-axis and the z-axis as defined by the maneuvering system; further wherein the data processing system is adapted to convert the commands of motions relative to the FOVx-axis, FOVy-axis, FOVz-axis to commands of motions relative to the x-axis, the y-axis and the z-axis.

It is another object of the present invention to disclose the method as defined above, additionally comprising a step of providing the control means comprising at least one joystick unit in communication with the maneuvering system, adapted to operate the maneuvering system.

It is another object of the present invention to disclose the method as defined above, additionally comprising a step of providing the joystick unit wearable by a user of the system.

It is another object of the present invention to disclose the method as defined above, additionally comprising a step of coupling the joystick unit to at least one surgical tool used in the medical procedure.

It is another object of the present invention to disclose the method as defined above, additionally comprising a step of selecting the at least one surgical tool to be the endoscope.

It is another object of the present invention to disclose the method as defined above, additionally comprising a step of controlling the movement of the joystick such that the movement of the joystick is proportional to the movement of the endoscope.

It is another object of the present invention to disclose the method as defined above, additionally comprising a step of selecting the joystick unit to be a force joystick.

It is another object of the present invention to disclose the method as defined above, additionally comprising a step of selecting the joystick unit comprising a base and lever coupled to the base, such that movement of the lever results in movement of the endoscope; further wherein the movement of the lever is proportional to the movement of the endoscope.

It is another object of the present invention to disclose the method as defined above, additionally comprising a step of selecting the joystick unit comprising a base and a button jointly connected to the base, such that movement of the button results in movement of the endoscope; further wherein the movement of the button is proportional to the movement of the endoscope.

It is another object of the present invention to disclose the method as defined above, additionally comprising a step of selecting the joystick unit comprising a touchscreen, such that a touch and a movement on the touchscreen results in movement of the endoscope; further wherein the touch and movement on the touchscreen is proportional to the movement of the endoscope.

It is another object of the present invention to disclose the method as defined above, additionally comprising a step of selecting the joystick unit comprising at least one sound sensor, adapted to sense predetermined sound patterns; the joystick unit adapted to operate the maneuvering system based on the predetermined sound patterns.

It is another object of the present invention to disclose the method as defined above, additionally comprising a step of providing the system adapted to direct the endoscope by using image information shown on the video screen without the help of assistants.

It is another object of the present invention to disclose the method as defined above, additionally comprising a step of, if the joystick unit's speed of motion is above a predetermined value, setting the endoscope's speed to be at the predetermined value.

It is another object of the present invention to disclose the method as defined above, additionally comprising a step of providing the joystick unit additionally comprising n sensors, where n is an integer larger than one.

It is another object of the present invention to disclose the method as defined above, additionally comprising a step of selecting the sensors from a group consisting of a motion sensor, a heat sensor, an electric sensor, a sound sensor, a pressure sensor, an optical sensor and any combination thereof.

It is another object of the present invention to disclose the method as defined above, additionally comprising a step of activating at least one of the n sensors in case of power failure.

It is another object of the present invention to disclose the method as defined above, additionally comprising a step of activating at least one of the n sensors when the system is connected to power.

It is another object of the present invention to disclose the method as defined above, additionally comprising a step of characterizing the joystick unit by an external surface.

It is another object of the present invention to disclose the method as defined above, additionally comprising a step of adapting the at least one motion sensor to detect motion upon the external surface.

It is another object of the present invention to disclose the method as defined above, additionally comprising a step of adapting the at least one motion sensor to detect motion perpendicular to the external surface.

It is another object of the present invention to disclose the method as defined above, additionally comprising a step of adapting the at least one heat sensor to sense temperatures in the range of about 35 to about 42 degrees.

It is another object of the present invention to disclose the method as defined above, additionally comprising a step of adapting the system to enable maneuvering of the endoscope at such times as the at least one heat sensor senses temperatures in the range of about 35 to about 42 degrees.

It is another object of the present invention to disclose the method as defined above, additionally comprising a step of adapting the at least one heat sensor to provide thermal image; the at least one heat sensor is coupled to a processing unit adapted to provide the system user with the thermal image.

It is another object of the present invention to disclose the method as defined above, additionally comprising a step of adapting the system to enable maneuvering of the endoscope at such times as analysis of the image by the processing unit detects the image of a human hand; further wherein the system is adapted to prevent maneuvering of the endoscope at such times when the analysis of the image by the processing unit fails to detect an image of a human hand.

It is another object of the present invention to disclose the method as defined above, additionally comprising a step of adapting the at least one electric sensor to sense power failure.

It is another object of the present invention to disclose the method as defined above, additionally comprising a step of adapting the at least one electric sensor to sense electric conductivity of a human body.

It is another object of the present invention to disclose the method as defined above, additionally comprising a step of adapting the system to enable maneuvering of the endoscope at such times when the sensor senses the conductivity of the subject's body; further wherein the system is adapted to prevent maneuvering of the endoscope at such times as the sensor fails to sense the conductivity of the subject's body.

It is another object of the present invention to disclose the method as defined above, additionally comprising a step of adapting the at least one sound sensor to sense at least one predetermined sound pattern.

It is another object of the present invention to disclose the method as defined above, additionally comprising a step of maneuvering the endoscope according to the at least one predetermined sound pattern sensed by the at least one sound sensor.

It is another object of the present invention to disclose the method as defined above, additionally comprising a step of adapting the at least one pressure sensor to sense pressure applied to the joystick unit.

It is another object of the present invention to disclose the method as defined above, additionally comprising a step of affecting the maneuvering system in response to the pressure sensed by the at least one pressure sensor in a manner selected from a group consisting of: when the pressure sensed by the at least one pressure sensor is above a predetermined value, the maneuvering system is activated; when the pressure sensed by the at least one pressure sensor is above a predetermined value, the maneuvering system is de-activated; and when the pressure sensed by the at least one pressure sensor is below a predetermined value, the maneuvering system is de-activated.

It is another object of the present invention to disclose the method as defined above, additionally comprising a step of adapting the at least one optical sensor to sense visual changes according to at least one predetermined visual pattern.

It is another object of the present invention to disclose the method as defined above, additionally comprising a step of maneuvering the endoscope according to the at least one predetermined visual pattern.

It is another object of the present invention to disclose the method as defined above, additionally comprising a step of providing an interface system adapted to enable communication between the joystick unit and the maneuvering system.

It is another object of the present invention to disclose the method as defined above, additionally comprising a step of providing the communication means comprising a member selected from a group consisting of a wired communication means, a wireless communication means and any combination thereof.

It is another object of the present invention to disclose the method as defined above, additionally comprising a step of providing the maneuvering system comprising at least one second joystick unit adapted to zoom the endoscope by means of the maneuvering system.

It is another object of the present invention to disclose the method as defined above, additionally comprising a step of providing the second joystick unit wearable by the system user.

It is another object of the present invention to disclose the method as defined above, additionally comprising a step of coupling the second joystick unit to at least one surgical tool.

It is another object of the present invention to disclose the method as defined above, additionally comprising a step of selecting the at least one surgical tool to be the endoscope.

It is another object of the present invention to disclose the method as defined above, additionally comprising a step of providing a single device comprising the joystick unit and the second joystick unit.

It is another object of the present invention to disclose the method as defined above, additionally comprising a step of adapting the at least one joystick unit to control and to direct the endoscope on the surgical tool via the maneuvering system.

It is another object of the present invention to disclose the method as defined above, additionally comprising a step of selecting the at least one surgical tool by activating the at least one joystick unit; further wherein the activation of the at least one joystick unit is obtained by depression of the joystick unit, voice activating the same, prolonged depression on the same, double clicking on the same and any combination thereof.

It is another object of the present invention to disclose the method as defined above, additionally comprising a step of providing
  a. at least one wearable operator comprising at least one wireless transmitter, adapted to transmit a signal once the at least one wearable operator is activated; the at least one wearable operator is either wire or wirelessly in communication with at least one surgical instrument;
  b. at least one wireless receiver; adapted to receive the signal sent by the transmitter;
  c. at least one laparoscopy computerized system, in communication with the wireless receiver, adapted to provide a visual onscreen depiction of the at least one instrument to be selected following the activation of the at least one wearable operator; and,
  d. at least one video screen; wherein the system is adapted to control and to direct the endoscope via the laparoscopy computerized system and the maneuvering system on the instrument to be selected following the activation of the at least one wearable operator.

It is another object of the present invention to disclose the method as defined above, additionally comprising a step of providing the communication between the at least one of the wearable operators and the instrument to be either wired or wireless coupling.

It is another object of the present invention to disclose the method as defined above, additionally comprising a step of providing the wearable operator to be worn by the surgeon on a predetermined body part.

It is another object of the present invention to disclose the method as defined above, additionally comprising a step of selecting the predetermined body part from a group consisting of: the hand of the surgeon, at least one of the fingers of the surgeon, the thigh of the surgeon, the neck of the surgeon, at least one of the legs of the surgeon, the knee of the surgeon, the head of the surgeon and any combination thereof.

It is another object of the present invention to disclose the method as defined above, additionally comprising a step of selecting the shape of the wearable operator from a group consisting of a ring, a bracelet and any combination thereof.

It is another object of the present invention to disclose the method as defined above, additionally comprising a step of coupling the wearable operator to a predetermined location on the instrument by means of an adaptor.

It is another object of the present invention to disclose the method as defined above, additionally comprising a step of adjusting the wearable operator so as to fit the predetermined location of the different instruments, each of which is characterized by a different size and shape.

It is another object of the present invention to disclose the method as defined above, additionally comprising a step of providing the wearable operator comprising a body having at least two portions at least partially overlapping each other; the two portions are adapted to grasp and hold either the instrument or the predetermined body part there-between, such that a tight-fit coupling between the two portions and the instrument or the predetermined body part is obtained.

It is another object of the present invention to disclose the method as defined above, additionally comprising a step of providing one of the two portions rotationally movable relative to the other, such that when the wearable operator is coupled to the instrument, fine-tuned movement of the two body portions is obtainable so as to provide the tight-fit coupling between the two portions and the instrument or the predetermined body part.

It is another object of the present invention to disclose the method as defined above, additionally comprising a step of providing the two portions rotationally movable relative to each other, such that when the wearable operator is coupled to the instrument, fine-tuned movement of the two body portions is obtainable so as to provide the tight-fit coupling between the two portions and the instrument or the predetermined body part.

It is another object of the present invention to disclose the method as defined above, additionally comprising a step of providing the wearable operator comprising (a) at least one flexible and stretchable strip; and (b) loop-closing means adapted to close a loop with the at least one flexible and stretchable strip; the at least one flexible and stretchable strip and the loop-closing means are provided so as to fit the wearable operator to at least one selected from a group consisting of (a) the predetermined location of the different instruments; (b) the predetermined body part of the surgeon, each of which is characterized by a different size and shape.

It is another object of the present invention to disclose the method as defined above, additionally comprising a step of making the flexible and stretchable strip of material selected from a group consisting of silicone, rubber and any combination thereof.

It is another object of the present invention to disclose the method as defined above, additionally comprising a step of adapting the wireless transmitter to locate the position of at least one of the instruments.

It is another object of the present invention to disclose the method as defined above, additionally comprising a step of selecting the at least one instrument by activating the at least one wearable operator; further wherein the activation of the at least one wearable operator is obtained by depression on a predetermined location in the wearable operator, voice activating the same, prolonged depression on the same, double clicking on the same and any combination thereof.

It is another object of the present invention to disclose the method as defined above, additionally comprising a step of the laparoscopy computerized system using image information shown on the video screen to direct the endoscope without the help of assistants.

It is another object of the present invention to disclose the method as defined above, additionally comprising a step of providing the conventional laparoscopy computerized system comprising at least one surgical instrument spatial location software, adapted to locate the 3D spatial position of the at least one instrument; further wherein the conventional laparoscopy computerized system comprises at least one automated assistant maneuvering system; the automated assistant maneuvering system is coupled to the endoscope and is adapted to direct the endoscope to the at least one instrument, the instrument selected following the activation of the at least one wearable operator.

It is another object of the present invention to disclose the method as defined above, additionally comprising a step of matching each transmitted signal from the wearable operator and the wireless transmitter to at least one of the instruments.

It is another object of the present invention to disclose the method as defined above, additionally comprising a step of varying velocity of the endoscope's tip according to the closeness of the endoscope tip to the object in the center of the field of view of the camera.

It is another object of the present invention to disclose the method as defined above, additionally comprising a step of setting velocity of the endoscope's tip proportional to the distance between the endoscope's tip and the object in the center of the FOV.

It is another object of the present invention to disclose the method as defined above, additionally comprising a step of selecting the endoscope to be an articulated endoscope.

It is another object of the present invention to disclose the method as defined above, additionally comprising a step of controlling articulation of the articulated endoscope by the system.

It is another object of the present invention to disclose the method as defined above, additionally comprising a step of controlling articulation of the articulated endoscope independently of the system.

It is another object of the present invention to disclose the method as defined above, additionally comprising a step of characterizing the endoscope by a pivoting point.

It is another object of the present invention to disclose the method as defined above, additionally comprising a step of adapting the system to correct automatically for changes in the pivoting point of the endoscope.

It is another object of the present invention to disclose the method as defined above, additionally comprising a step of coupling the control means to the endoscope maneuvering system via a link selected from a group consisting of: a wired link, a wireless link, and any combination thereof.

It is another object of the present invention to disclose the method as defined above, additionally comprising a step of adapting the system to maintain the center of the FOV unchanged during zooming, independent of the angle of the endoscope's tip with respect to the longitudinal axis of the endoscope.

It is another object of the present invention to disclose the method as defined above, additionally comprising a step of adapting the system to maintain the angle of the FOV unchanged during zooming.

It is another object of the present invention to disclose the method as defined above, additionally comprising a step of adapting the system to maintain the angle of the FOV unchanged during lateral motion.

It is another object of the present invention to disclose the method as defined above, additionally comprising a step of adapting the system such that the angle of the endoscope's tip with respect to the longitudinal axis of the endoscope is not predetermined.

It is another object of the present invention to disclose the method as defined above, additionally comprising a step of adapting the control means to be worn in conjunction with at least some portion of the body of a user.

It is another object of the present invention to disclose the method as defined above, additionally comprising a step of selecting the portion of the body from the group consisting of finger, arm, chest, head, neck, waist, hips, thighs, legs, and any combination thereof.

It is another object of the present invention to disclose the method as defined above, additionally comprising a step of adapting the system to automatically maintain the image unchanged by maneuvering the endoscope in response to uncommanded motion.

It is another object of the present invention to disclose the method as defined above, additionally comprising a step of adapting the system to automatically maintain the horizon of the image unchanged by maneuvering the endoscope in response to uncommanded motion.

It is another object of the present invention to disclose the method as defined above, additionally comprising a step of adapting the system to automatically maintain the horizon of the image unchanged during maneuvering of the endoscope.

It is another object of the present invention to disclose the method as defined above, additionally comprising a step of adapting the system to track an object.

It is another object of the present invention to disclose the method as defined above, additionally comprising a step of adapting the system to retain the object in the center of the FOV.

It is another object of the present invention to disclose the method as defined above, additionally comprising a step of selecting the object from a group consisting of an organ, a vein, an artery, a ligament, a membrane, fat tissue, a medical tool, a scalpel, a forceps, a retractor, a swab, a clamp, and a needle.

It is another object of the present invention to disclose the method as defined above, additionally comprising a step of adapting the system to maneuver a controlled object selected from a group consisting of an endoscope and a surgical tool in a manner selected from a group consisting of a discrete movement, a continuous movement and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1A-B schematically illustrates the effect of differences in alignment of axes fixed to the maneuvering system and axes fixed to the camera on motion of the image as seen by an endoscope for a conventional system.

DETAILED DESCRIPTION OF THE PREFERRED EMBODIMENTS

Figure 1A:
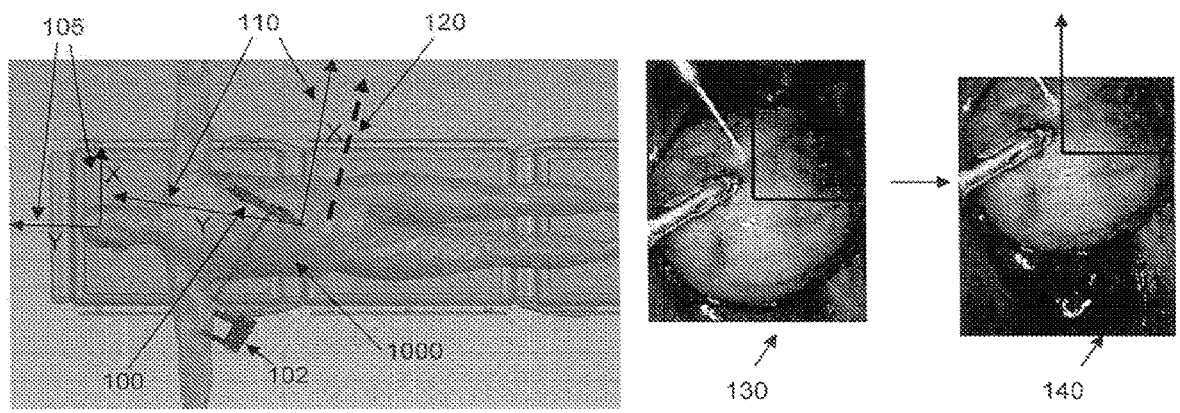

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for automatic control of an endoscope.

The present invention provides a system for controlling an endoscope, comprising an endoscope adapted to provide real time images of a field of view (FOV), where the FOV characterizes a spatial location, and the endoscope is characterized by a spatial location; a maneuvering system for maneuvering the endoscope in at least two DOF controlling means adapted to receive commands of motions to maneuver the endoscope; and a data processing system in communication with the control means, adapted to instruct the maneuvering system to maneuver the endoscope according to the commands of motions; wherein the data processing system instructs the maneuvering system to maneuver the endoscope according to commands of motions relative to the spatial location of the FOV as displayed in the real time image, without reference to the spatial location or the spacial orientation of the endoscope.

The present invention also provides a system for controlling an endoscope, comprising an endoscope adapted to provide real time images of a FOV, where the FOV characterizes a spatial location, and the endoscope is characterized by a spatial location; means adapted to determine the angle of the endoscope's tip; a maneuvering system for zooming the endoscope; a maneuvering system for lateral motion of the endoscope; controlling means adapted to receive commands to zoom the endoscope; a data processing system in communication with the endoscope, adapted to determine the spatial position of the center of the FOV; a data processing system in communication with the control means, adapted to instruct the maneuvering system to zoom the endoscope and to instruct the maneuvering system to maneuver the endoscope relative to the spatial location of the FOV as displayed in the real time image, without reference to the spatial location of the endoscope; wherein the zoom mechanism maintains the center of the image constant and adjusts the position of the endoscope so as to keep the center of the image constant.

The present invention also provides a system for controlling a camera, comprising a camera adapted to provide real time images of a FOV, where the FOV characterizes a spatial location, and the camera is characterized by a spatial location; a maneuvering system for maneuvering the camera in at least two DOF; controlling means adapted to receive commands of motions to maneuver the camera; a data processing system in communication with the control means, adapted to instruct the maneuvering system to maneuver the camera according to the commands of motions; wherein the data processing system instructs the maneuvering system to maneuver the camera according to the commands of motions relative to the spatial location of the FOV as displayed in the real time image, without reference to the spatial location of the camera.

The system of the present invention can be used for discrete movements, for non-limiting example, for repositioning an endoscope so that its FOV encompasses a different part of an organ. The system of the present invention can also be used to continuous movement, such as, for non-limiting example, continuously repositioning the endoscope tip to correct for movement caused by the patient's breathing, thereby giving the surgeon to a steady view of the desired position within the surgical field, independent of movements of the penetration point or movements of the laparoscope relative to the penetration point.

The term 'camera' hereinafter refers to an image acquiring element. Examples of a camera include, but are not limited to, a CCD array and an electromagnetic system such as a TV camera.

The term 'endoscope tip' hereinafter refers to the end of the endoscope that is inside the patient, the lens-side tip of the endoscope. The camera is attached to the other side of the endoscope, outside of the patient's abdomen.

The term 'uncommanded motion' hereinafter refers to motion that is not commanded by a user. Examples of uncommanded motion are, but are not limited to, breathing by the patient, compaction of the tissues against which the endoscope is resting, shifting of the tissues against which the endoscope is resting, and creep in the endoscope maneuvering system.

The term 'constant' hereinafter refers to a non-varying, fixed in place and space element.

The term 'constant axis' hereinafter refers to a non-varying, predetermined, fixed in place and space axis. According to a preferred embodiment of the present invention, the maneuvering system's axes (refers hereinafter as x-axis, y-axis and z-axis) are constant and do not change all through the procedure.

The terms 'FOVx-axis', 'FOVy-axis' and 'FOVz-axis' hereinafter refers to the axes of a 3 dimensional coordinate system fixed with respect to the camera and, therefore, the camera image. The camera image is two dimensional, so that it will define the directions of two of the three axes FOVx-axis, FOVy-axis and FOVz-axis, with the third axis being perpendicular to the other two.

The term 'FOV coordinate system' to the 3 dimensional coordinate system defined by the FOVx-axis, FOVy-axis and FOV-z axis.

The term 'horizon' hereinafter refers to the line defining the edge of the field of view of a camera. In a true camera pan, the edge of the field of view remains on the horizon of previous fields of view.

The term 'field of view' (FOV) hereinafter refers to the field visible to the camera.

The term 'degree of freedom' (DOF) hereinafter refers to an independent parameter which defines the configuration of the system. As a non-limiting example, in a system where motion can occur in two perpendicular directions, the system has two DOF's.

The term 'about' hereinafter refers to approximately 10%.

The term 'screen' hereinafter refers to a device adapted to show movable images. 'Screen' and 'video screen' will be used interchangeably herein.

The present invention is intended to provide an intuitive control system for an endoscopic apparatus adapted for laparoscopic surgery. The surgery can be in the abdomen, it can be ENT surgery or orthopedics and the surgery can be with or without an endoscope. In operations without an endoscope, the maneuvering system can control the movement of a surgical tool.

Figure 1B:
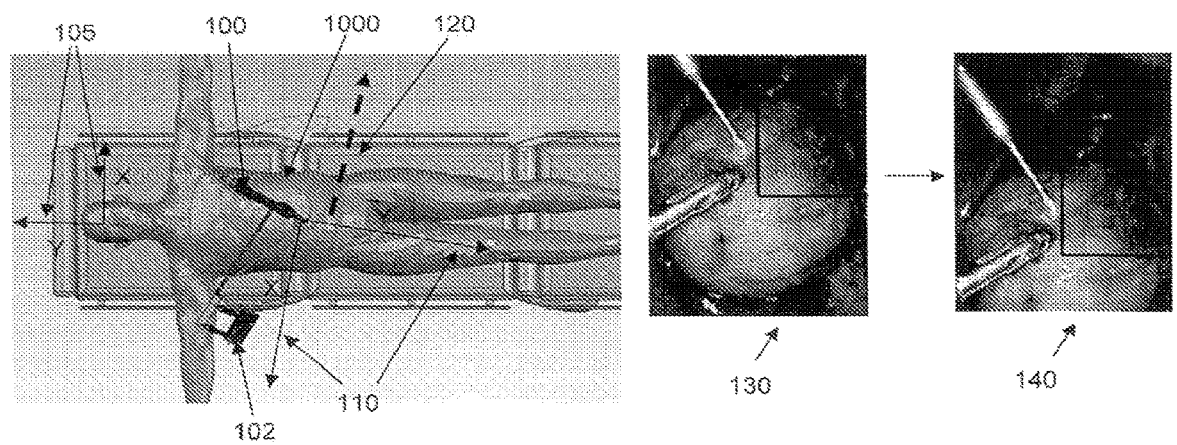

FIG. 1 schematically illustrates, in an out-of-scale manner, a patient (1000) with an endoscope (100) in the abdomen. The control and maneuvering system (102) for the endoscope is also shown. In conventional endoscopic control systems, the axes (105) used by the endoscope (100) control system to modify the position of the tip of the endoscope are fixed in space. If the body of the patient (1000) is used as an exemplary referent, such that "left" is toward the patient's left, "forward" is toward the patient's head and "up" is in the direction of removal from the patient, and similarly for "right", "back" and "down", then, if the surgeon commands a move to the "right", the lens-side tip of the endoscope (the end inside the patient) will move towards the patient's right (120) no matter what the orientation of the endoscope, thereby moving the center of the field of view towards the patient's right (it should be noted that the external end of the endoscope, i.e., the camera side; will move to the left). In FIGS. 1A and 1B, an image of the patient, with axes superimposed, is the leftmost image in the figure, the image before the endoscope moves (130) is the central image in the figure, while the image after the endoscope has moved (140) is the rightmost image in the figure.

In the example shown in FIGS. 1A and 1B, the image axes 105 show exemplary image axes, as described above, superimposed for convenience on the head of the patient. Exemplary maneuvering system axes 110 are shown superimposed for convenience superimposed on the penetration point of the endoscope for the maneuvering system 102.

For the system shown in FIG. 1, a movement of the maneuvering system along an axis moves the internal (lens-side) end of the endoscope in the direction of the axis.

In a conventional endoscopic control system, the control system does not know the relative positions of the image axes and the maneuvering system axes. If the control system receives a command to move, for example, right, the control system commands the maneuvering system to move right. However, the movement of the field of view can be in any direction, depending on the relative orientations of the image axes and the maneuvering system axes. For example, if the image axes (110) are parallel to the maneuvering system axes (105), as in FIG. 1A, then the center of the field of view (FOV) will move in the same direction as the motion of the lens-side tip of the endoscope (FIG. 1A, 130 and FIG. 1A, 140). However, if the image axes (110) are rotated 180° relative to the maneuvering system axes (105), then the center of the field of view will move in the opposite direction from the direction of motion of the lens-side endoscope tip (FIG. 1B, 130 and FIG. 1B, 140). If the image axes are at some other angle relative to the maneuvering system axes, the center of the field of view will move in yet another direction. Thus, in conventional systems, the surgeon is forced to remember the relative angles of the two sets of axes in order to have the endoscope tip move in a desired direction, and automatic retention unchanged of the field of view in the face of uncommanded motions is virtually impossible, as corrective movement relative to the image axes would move the endoscope according to the maneuvering system axes, resulting in movement in an undesired direction.

In the system of the present invention, the image axes, not the maneuvering system axes, are used as the control system axes, so that a command to move in the direction of the X axis moves the field of view in the direction of the image X axis by moving the endoscope camera-side tip in the direction of the image X axis, as shown in FIG. 1A. The maneuvering is, at all times, relative to the camera image (FOV) axes, which change direction as the camera is manipulated, not the constant maneuvering system axes. Therefore, in the system of the present invention, it is impossible for the scenario shown in FIG. 1B to occur, thus reducing the probability of operator error or wasted time during the operation and making possible automatic retention unchanged of the field of view in the face of uncommanded motions.

Figure 2A:
FIGS. 2A-D, 3A-D and 4A-C schematically illustrate the effect of differences in alignment of axes fixed to the maneuvering system and axes fixed to the camera on motion of the image as seen by an endoscope for the present system.
Figure 2B:
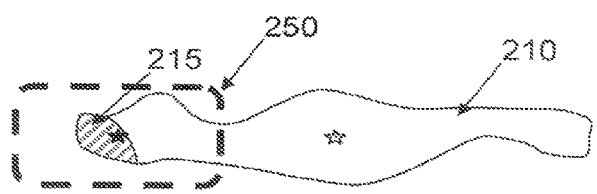
Figure 2C:
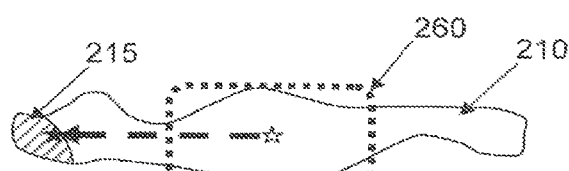
Figure 2D:
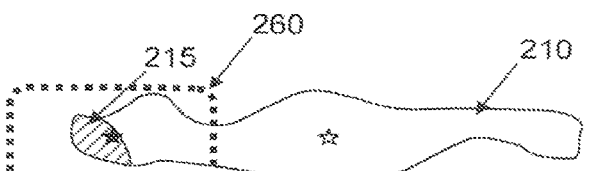
Figure 3A:
Figure 3B:
Figure 3C:
Figure 3D:
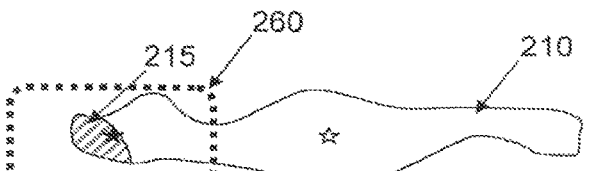

In reference to FIGS. 2 and 3, an example is shown, for the present system of the relationship between movement of the FOV and movement of the maneuvering system, FIGS. 2A and B and FIGS. 3A and B illustrate the "screen side", showing the part of the organ 210 displayed on the screen (dashed box 250) and, for clarity, the invisible parts of organ 210, while FIGS. 2C and D and FIGS. 3C and D illustrate the "lens side", showing the organ 210 and the field of view of the lens (dotted box 260). In FIGS. 2 and 3, the white star in the center of the object illustrates the center of the image before maneuvering and the black star in the striped region of the object illustrates the center of the image after maneuvering, while the dashed arrow indicates the direction of movement. In both FIGS. 2 and 3, before maneuvering, the FOV displayed on the screen shows approximately the center of the organ 210, with the center of the FOV marked by the white star, and the user desires to see the end portion 215 of the organ 210, and to have the FOV centered on the black star.

In FIG. 2, the orientation of the camera and the orientation of the maneuvering system are the same, while, in FIG. 3, the camera is inverted relative to the maneuvering system.

In FIG. 2A, the user desires to view the end 215 of the organ. Therefore, the user commands the endoscope to move left (dotted arrow) in order to move the FOV from the center of the organ (white star) to the end 215 of the organ. FIGS. 2C and D indicate the manner in which this is carried out. In FIG. 2C, the lens images (260) the center of the organ (white star). In order to move the FOV to the end of the organ 215, the maneuvering system maneuvers the endoscope so as to move the lens tip of the endoscope to the left (dotted arrow). After the maneuver, (FIG. 2D) the lens images the end of the organ 215, with the image centered on the black star. FIG. 2B shows the image as shown on the screen after the move. The end of the organ (215) is in the FOV and the black star is at the center of the FOV.

In FIG. 3A, the camera axes are inverted relative to the maneuvering system axes. The user desires to view the end 215 of the organ. Therefore, the user commands the endoscope to move right (dotted arrow) in order to move the FOV from the center of the organ (white star) to the end 215 of the organ. FIGS. 3C and D indicate the manner in which this is carried out. In FIG. 3C, the lens images (260) the center of the organ (white star). In order to move the FOV to the end of the organ 215, the maneuvering system maneuvers the endoscope so as to move the lens tip of the endoscope to the left (dotted arrow). After the maneuver, (FIG. 3D) the lens images the end of the organ 215, with the image centered on the black star. FIG. 3B shows the image as shown on the screen after the move. The end of the organ (215) is in the FOV and the black star is at the center of the FOV.

Similarly, if the camera axes are rotated 90° clockwise relative to the maneuvering system axes, the user will command a motion toward the top of the page in order to move the FOV from the center of the organ to the end 215; the maneuvering system will move the lens tip to the left.

Figure 4A:
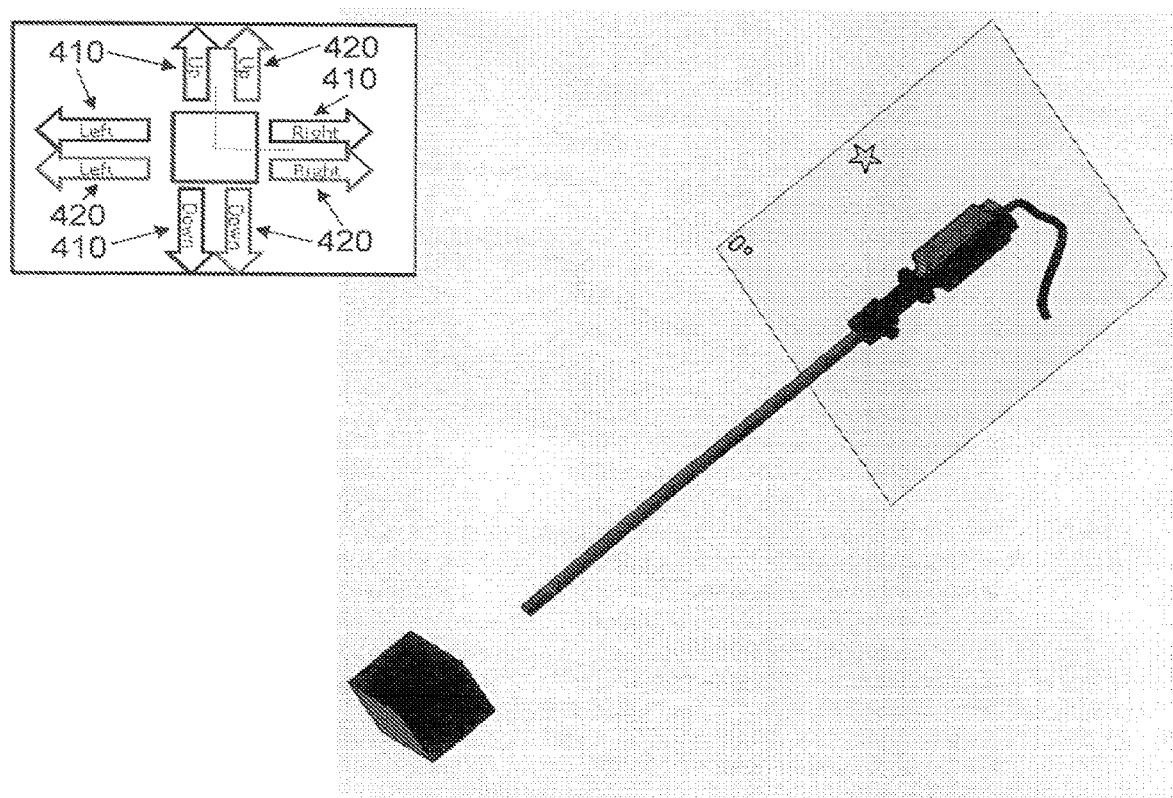
Figure 4B:
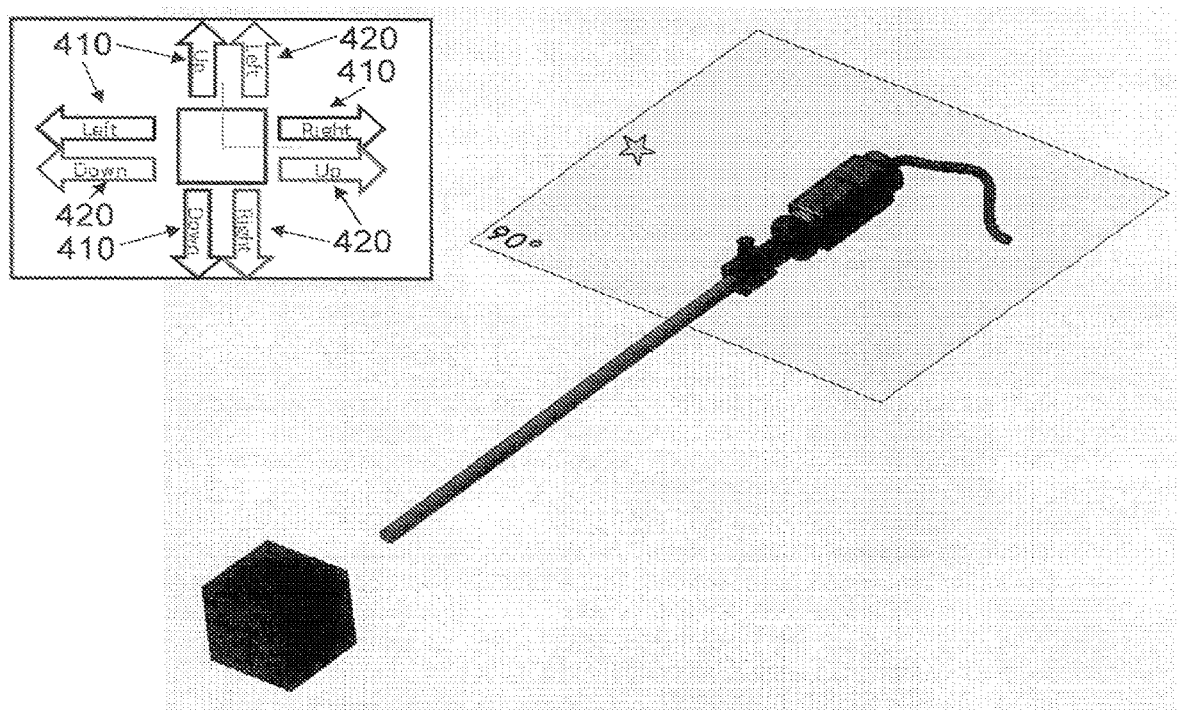
Figure 4C:
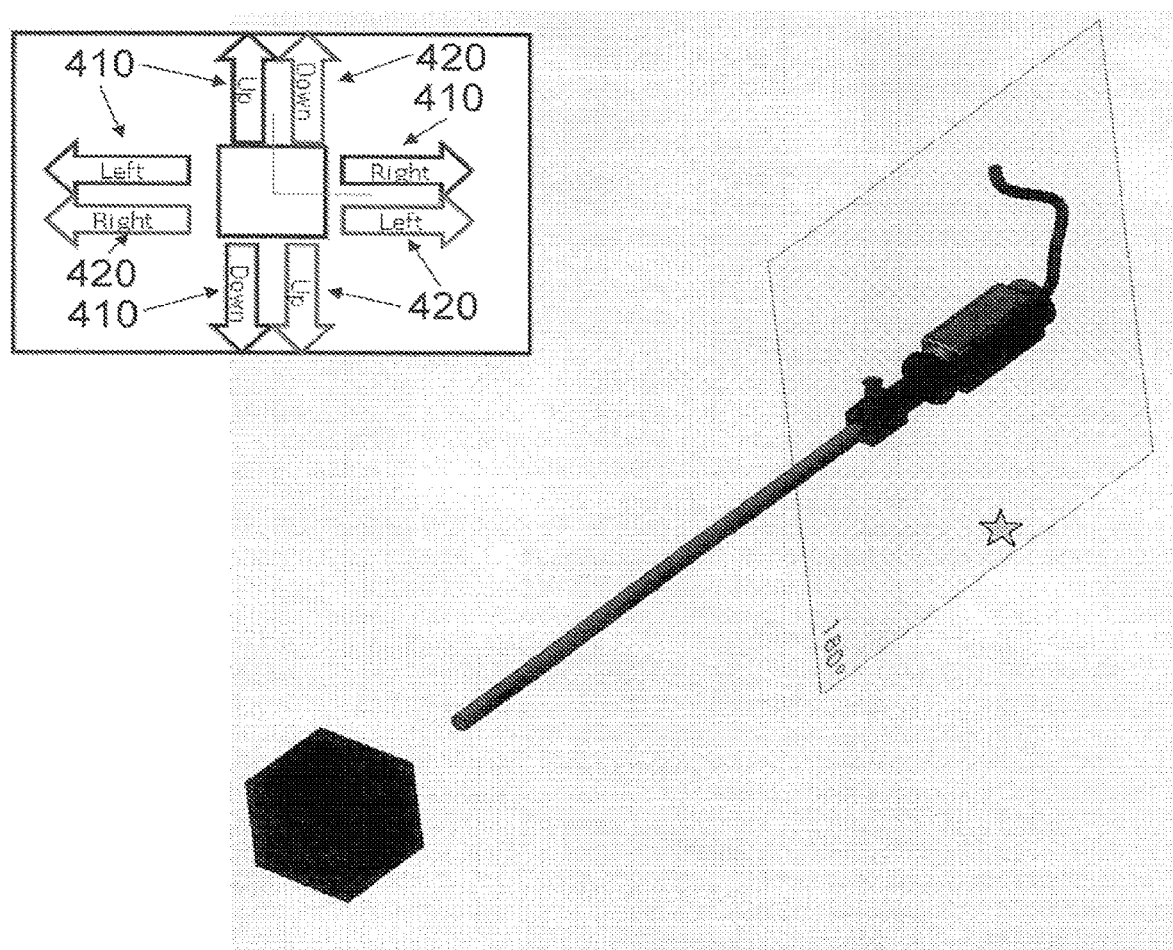

FIGS. 4A-C show another view of the effects of rotating the camera relative to the maneuvering system. In FIGS. 4A-C, directions relative to the image seen on the screen are referred to by the number 410, while directions relative to the maneuvering system are referred to by the number 420, In FIG. 4A, the FOV (camera) axes 410 and the maneuvering system axes 420 are aligned (0° rotation with respect to each other), so that a command to move the FOV up (410, lefthand arrow on top, in the direction of the star) will cause the maneuvering system to move the endoscope such that the lens tip moves up (420, righthand arrow at top), and similarly for the other directions of movement.

In FIG. 4B, the FOV axes and the maneuvering system axes are perpendicular to each other (at 90°). In this case, commanding the FOV to move up (410, lefthand arrow on top, in the direction of the star) requires the maneuvering system to move left (420, righthand arrow at top) in order to accomplish this, and similarly for the other directions of movement.

In FIG. 4C, the FOV axes and the maneuvering system axes are rotated 180° to each other. In this case, commanding the FOV to move up (410, lefthand arrow on top, in the direction of the star) requires the maneuvering system to move down (420, righthand arrow at top) in order to accomplish this, and similarly for the other directions of movement.

It should be noted that, for this system, as shown in FIGS. 2 to 4, the same physical movement of the maneuvering system, to accomplish the same change in the position of the endoscope relative to the patient's body (in this case, to the left) can be commanded by different commands (left, right, up or down), depending on the orientation of the camera relative to the maneuvering system and the patient's body. Physical reality does not depend on the orientation of the camera. However, the perception of how to change the physical reality to achieve the desired result will depend on the orientation of the camera.

Figure 5:
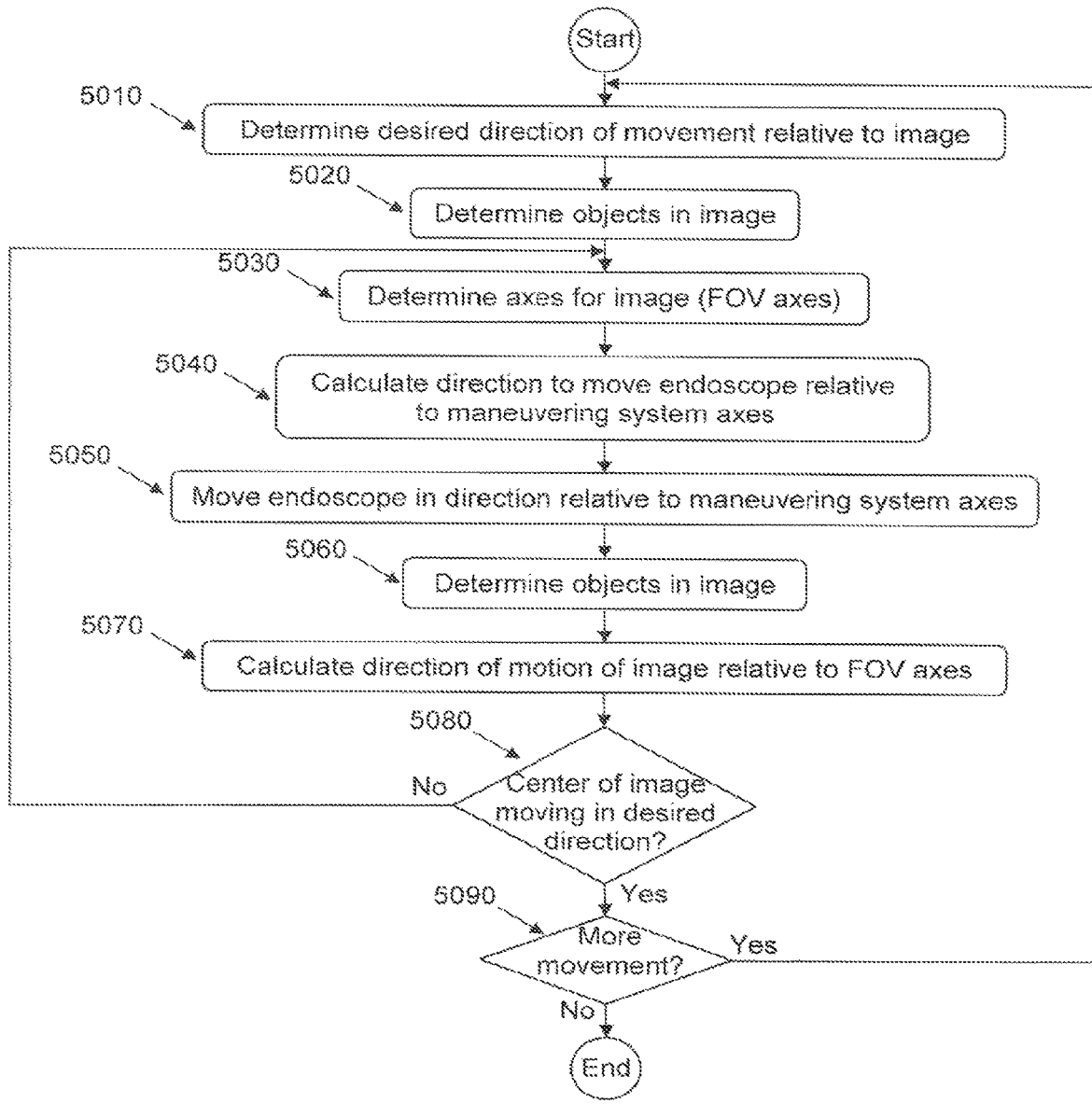
FIG. 5 schematically illustrates a flow chart of control of movement of the endoscope.

In an embodiment of the system of the present invention, a control data processing system estimates the position of the lens-side tip of the endoscope and its angular orientation, based on at least one of (a) sensors in the system and (b) image analysis of the image of the field of view, and calculates the motions of the endoscope necessary to enable the endoscope tip to move in the commanded direction. Sensors in the system can be, but are not limited to, accelerometers, gyroscopic sensors, or both. FIG. 5 illustrates a flow chart of an embodiment of a controlling means to enable the system to move the field of view in the desired direction. When the user commands a motion, the software determines the desired direction of motion (5010), relative to the displayed image (FOV axes). The motion can be commanded by means exemplified by, but not limited to, vocal commands, movement of a joystick, movement of a lever, pressure on a button, movement parallel to a prepared surface, movement perpendicular to a prepared surface, entry of a command via a keyboard, entry of a command via a touchscreen and any combination thereof. The data processing system then determines the center of the camera image (5020) and, if necessary, the objects in the camera image are determined using an image processing system. The data processing system determines the directions of the FOV axes relative to the maneuvering system axes, which are fixed in space (5030). From the desired direction relative to the FOV axes, and the relative orientations of the FOV axes and the maneuvering system axes, the direction relative to the maneuvering system axes in which to move the endoscope tip is calculated (5040), and the endoscope tip is moved in the calculated direction (5050). During motion, objects in the image (5060) are found and a comparison made between their present location in the image and their location in a previous image from which the direction of motion of the field relative to the FOV is found (5070) and checked as to whether the center of the image is moving in the desired direction (5080). If necessary, the direction of motion is recalculated (5040-5070). Checks are made whether more motion is commanded (5090). If so, the cycle (5010-5090) repeats. If not, the cycle terminates.

In an embodiment of the system of the present invention, unlike in conventional systems, the controlling means maintains the center of the FOV during zoom independent of the tip lens angle. An advantage of controlling the zoom of the endoscope via a data processing system is that the tip lens angle does not need to be input to the data processing system, obviating a possible source of error In use, the endoscope pivots about a point on or near the surface of the skin of the skin of the patient. This pivot point can move for many reasons, including movement of the patient's body due to breathing, compaction of the tissues against which the endoscope is resting and shifting of the tissues against which the endoscope is resting. Such motion causes motion of the FOV of the endoscope and can also cause blurring of the image, both of which are undesirable. In preferred embodiments of the present system the system corrects for such uncommanded motion. In preferred embodiments of the system, the control data processing determines, either from sensors in the system or from the camera image, whether uncommanded motion of the image has occurred.

According to another embodiment of the present invention, the system can inform the user of any misalignment of the system.

Misalignment of the system may cause parasitic movement of the endoscope tip, where the endoscope tip does not move exactly in the expected direction. According to one embodiment of the system, the system comprises sensors (e.g., gyroscopes, accelerometers and any combination thereof) that calculate/estimate the position of the pivot point in real time in order to (a) inform the user of misalignment; or (b) calculate the misalignment so that the system can adjust its movement to prevent parasitic movement.

In some embodiments of the system, the rotational angle of the camera with respect to the endoscope is not fixed. In some variants of this embodiment, the camera need not be attached to or placed in communication with the endoscope at a predetermined angle. In other variants, the camera can rotate with respect to the endoscope's main longitudinal axis during use, thereby adding another degree of freedom to the movement of the image. In conventional systems, the lack of a predetermined rotational angle between the camera and the endoscope requires the surgeon to remember the occurring angle for the duration of the procedure.

In conventional systems, rotation of the camera with respect to the endoscope's main longitudinal axis during a procedure either requires the surgeon to correct the occurring angle "on the fly", in his head during the procedure, or requires the operating assistant to manually rotate the camera whenever necessary to return the camera to its initial angle.

With the system of the present invention, the initial angle and the changing angle due to rotation of the camera with respect to the endoscope's main longitudinal axis are automatically corrected by the system; for example, the surgeon or other operator will be unaware of the occurrence of rotations of the camera with respect to the endoscope's main longitudinal axis.

In some embodiments of the system, the rotational angle of the endoscope with respect to the maneuvering system is not fixed. In some variants of this embodiment, the endoscope can rotate around its main longitudinal axis.

Thus, in conventional systems, the lack of a predetermined rotational angle between the endoscope and the maneuvering system requires the surgeon to remember the occurring angle for the duration of the procedure.

In conventional systems, rotation of the endoscope's axis with respect to the maneuvering system's axes during a procedure either requires the surgeon to correct the occurring angle "on the fly", in his head during the procedure, or requires the operating assistant to manually rotate the endoscope whenever necessary to return the image to its initial angle.

With the system of the present invention, the initial angle and the changing angle due to rotation of the endoscope with respect to the maneuvering system's axes are automatically corrected by the system; for example, the surgeon or other operator will be unaware of the occurrence of rotations of the endoscope.

In preferred embodiments of the present system, the relationship between the maneuvering system axes and the FOV's coordinate axes, as determined either by sensors or from the camera image, is known and is updated in real time, so that the relationship is accurately known at all times.

The mathematical transformations which transform motion relative to one set of axes to motion relative to another set of axes are well known in the art.

Since, as the camera moves, the relationship between the FOV coordinate system axes and the maneuvering system axes is real-time updated, there is, at all times, a known transformation between the FOV's coordinate axes and the maneuvering system's axes, such that motion relative to the screen is accurately transformed, via the known relationship between the coordinate systems and the known mathematical transformations, into motion of the maneuvering system.

Examples of such a mathematical transformation are given below for a position vector defining a point in space in one Cartesian coordinate system to the position vector defining the same point in space in a second Cartesian coordinate system rotated with respect to the first.

In two dimensions, if a first Cartesian coordinate system is rotated by an angle θ with respect to the first and the vector connecting the origins of the coordinate systems is given by (a,b), then a position in space defined by the vector (x,y) in the first coordinate system is transformed into the vector (X,Y) in the second coordinate system by the equations:

$X = x \cos \theta - y \sin \theta - a$ $Y = x \sin \theta + y \cos \theta - b$

In three dimensions, if the second coordinate system is rotated by Euler angles, θ, ψ with respect to the first and the vector connecting the origins of the coordinate systems is given by (a,b,c), then the rotational transformation between (x,y,z) in the first coordinate system and (X,Y,Z) in the second coordinate system is:

$X = x \cos \theta \cos \psi + y(\cos \sin \psi + \sin \sin \theta \cos \psi) + z(\sin \sin \psi - \cos \sin \theta \cos \psi) - a$ $Y = -x \cos \theta \sin \psi + y(\cos \cos \psi - \sin \sin \theta \sin \psi) + z(\sin \cos \psi + \cos \sin \theta \sin \psi) - b$ $Z = x \sin \theta - y \sin \cos \theta + z \cos \cos \theta - c$ Many other such transformations are given in the art, including transformations between different types of coordinate system, such as, for non limiting example, Cartesian-to-cylindrical and Cartesian-to-polar, Different embodiments of the present invention can use different such mathematical transformations known in the art, and any such mathematical transformation can be used in embodiments fo the present invention. It is emphasized that the above mathematical transformation is given as a mere example. Other transformations are known in the art and are within the scope of the present invention.

In some embodiments of the system, the endoscope is rotated to keep the angle of the FOV (the horizon) constant since the FOV of the endoscope will rotate as the endoscope moves (parasitic horizon change). In these embodiments, the data processing system detects such rotations and counter-rotates the endoscope so as to ensure that there is no uncommanded rotation of the image (parasitic horizon change) seen by the user during motion of the endoscope.

In some embodiments, the order in which motions are made is chosen to minimize changes in the angle of the FOV (the horizon). In many endoscopes, motions along fixed arcs are combined to create an apparently smooth movement in a desired direction. In many embodiments, the design of the mechanical parts that enable motion are such that the endoscope's axis will tilt and the endoscope will rotate about its axis as the center of the endoscope body moves along the arc. For such endoscopes, the order in which such motions are combined can affect the amount of rotation of the FOV (the amount of change in the horizon) because motions beginning from different starting points affect the tilt and the rotation differently.

In conventional endoscopic control systems, motion of the endoscope occurs at a single speed. This speed as fairly fast so that the endoscope can be moved rapidly between locations that are well separated. However, this means that making fine adjustments so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves.

In some embodiments of the system of the present invention, the endoscope is an articulated endoscope, incorporating one or more joints or bendable sections. An example of an articulated endoscope is the Stryker Ideal Eyes™ HD articulating laparoscope. In an embodiment of the system with articulated endoscope, motion of the articulations is controlled independently of the data processing system controlling motion of the endoscope. The independent control can be either manual, with a member of the surgical operating team repositioning the joints as needed, or the independent control can be via a control system operating via a joystick, lever, button, vocal commands, a touchscreen, typing commands into a keyboard, or other control means. In a preferred embodiment, motion of the articulations is controlled as part of the data processing system controlling motion of the endoscope, providing seamless control of the system and the maximum flexibility for the surgeon in positioning the endoscope to provide the optimum field of view at any given stage in the operation.

Figure 6:
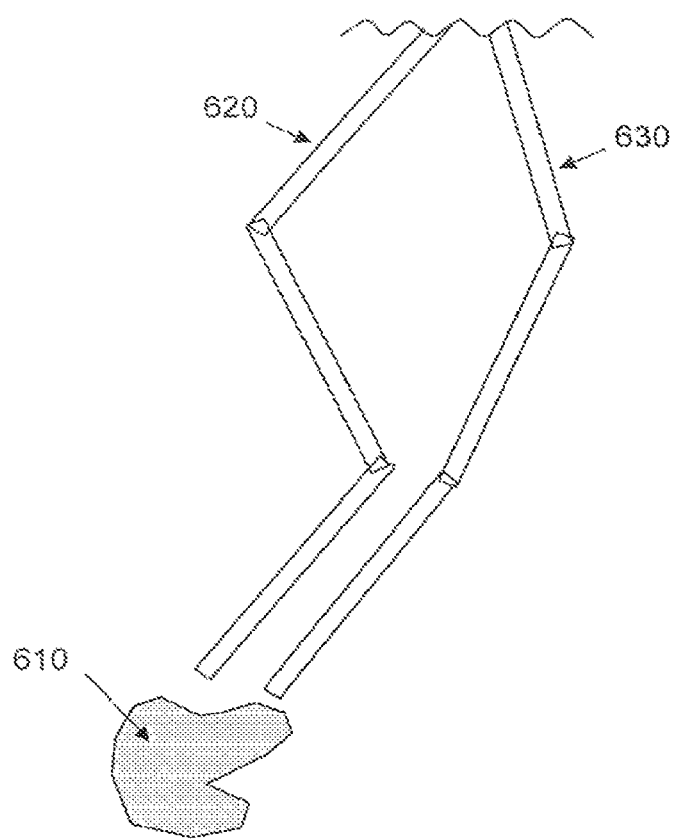
FIG. 6 schematically illustrates an articulated endoscope.

In embodiments of the system which include an articulated endoscope, there can be different configurations of the articulating endoscope that provide the same FOV at the same angle. An illustrative example of different configurations is shown in FIG. 6, which schematically illustrates an object (610) being viewed by an articulated endoscope. The two articulations are shown separated for clarity. On the left in the figure, the endoscope has one articulation (620), while, on the right, the endoscope has a different articulation (630), both providing a view of the object from the same distance and at the same angle.

In some embodiments, the system is enabled to track the motion of an object in the field of view, non-limiting examples of such an object being an organ, a tissue, at least a portion of a tool, tool's tip and any combination thereof. In these embodiments, the object of interest will remain in the center of the field of view, whatever motions are made by the body (for example, by breathing), or by the motion of the endoscope, for example, by slippage against the penetration point or by compression of the penetration point.

It should be noted that the system of the present invention can be used for discrete movements, for non-limiting example, for repositioning an endoscope so that its FOV encompasses a different part of an organ. The system of the present invention can also be used to continuous movement, such as, for non-limiting example, continuously repositioning the endoscope tip to correct for movement caused by the patient's breathing, thereby giving the surgeon to a steady view of the desired position within the surgical field, independent of movements of the penetration point or movements of the laparoscope relative to the penetration point.

It should be pointed out that the above disclosure relates to the use of the system with an endoscope for medical use, especially for operations inside the human body. However, the system provided above may also be adapted to use a camera, to observe objects of interest outside the body. In an embodiment of the system for non-medical use, the camera is used to observe objects of interest. As an illustrative example, such a maneuverable camera system can be used to observe animals such as bears or beavers inside their dens, where the maneuverable system could be used by an observer to track a given animal. Another illustrative use of such a system is to follow players on the soccer field during a game. An illustrative example of a medical use outside the body would be for physiotherapy, where more natural movement of a patient could be observed, by tracking the patient as she moves about a room, with the patient being at most minimally aware of being observed. In such systems, the camera can be mounted directly to the maneuvering system; it can be mounted on a tripod or other support system; or it can be mounted, as an endoscope is mounted, at the end of a long, slender support, where said support can be rigid or can be flexible or articulated.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for controlling an endoscope comprising steps of:
displaying in real time images of a field of view (FOV) acquired by an endoscope within a body cavity, said FOV defining at least two axes of a coordinate system fixed with respect to the camera and the displayed images, said at least two axes selected from a group consisting of FOVx-axis, FOVy-axis and FOVz-axis and any combination thereof, such that at least two axes selected from said FOVx-axis, said FOVy-axis, said FOVz-axis and any combination thereof are configured to be real time updated as at least a tip of said endoscope moves and said FOV changes;
receiving as user input FOV commands of motions to maneuver said at least a tip of said endoscope in real time in a desired direction, said FOV commands of motion being commands of motion relative to at least two axes selected from said FOVx-axis, said FOVy-axis and said FOVz-axis, as real time displayed in said image;
converting said FOV commands of motion to maneuvering system commands of motions for a maneuvering system configured to maneuver at least a tip of said endoscope in at least two DOF; said maneuvering system defining a constant x-axis, a constant y-axis and a constant z-axis, said maneuvering system commands of motion being commands of motion relative to said x-axis, said y-axis and said z-axis; and
causing said maneuvering system to maneuver said at least a tip of said endoscope according to said maneuvering system commands of motions.

2. The method according to claim 1, additionally comprising causing said maneuvering system to maneuver said at least a tip of said endoscope according to said commands of motions relative to at least two axes selected from said FOVx-axis, said FOVy-axis and said FOVz-axis and any combination thereof, as real time displayed in said image, regardless of the orientation of the camera within said endoscope with respect to said endoscope.

3. The method according to claim 1, additionally comprising causing said maneuvering system to maneuver said at least a tip of said endoscope according to said commands of motions relative to at least two axes selected from said FOVx-axis, said FOVy-axis and said FOVz-axis and any combination thereof, as real time displayed in said image, regardless of the angular orientation of the camera within said endoscope with respect to said endoscope.

4. The method according to claim 1, additionally comprising causing said maneuvering system to maneuver said at least a tip of said endoscope according to said commands of motions relative to at least two axes selected from said FOVx-axis, said FOVy-axis and said FOVz-axis and any combination thereof, as real time displayed in said image, regardless of the orientation of said endoscope with respect to said maneuvering system.

5. The method according to claim 1, wherein receiving FOV commands of motion comprises receiving FOV commands of motion from a manual movement controller.

6. The method according to claim 5, wherein receiving FOV commands of motion comprises receiving FOV commands of motion from a joystick.

7. The method according to claim 5, additionally comprising receiving from said manual movement controller commands of motions to maneuver at least one surgical tool within said FOV.

8. The method according to claim 5, wherein the converting step includes converting said commands of motions relative to said FOVx-axis, FOVy-axis, FOVz-axis to commands of motions relative to said x-axis, said y-axis and said z-axis, and wherein the method additionally comprises instructing said maneuvering system to maneuver said surgical tool according to said commands of motions relative to said FOVx-axis, FOVy-axis, FOVz-axis, as real time displayed in said image, regardless of said x-axis, said y-axis and said z-axis as defined by said maneuvering system.

\* \* \* \* \*